United States Patent [19]

Sheehan et al.

[11] Patent Number: 4,622,394

[45] Date of Patent: * Nov. 11, 1986

[54] OXYGEN ANALOGS OF CEPHALOSPORINS

[75] Inventors: John C. Sheehan, Lexington; Young S. Lo, Boston, both of Mass.

[73] Assignee: Massachusetts Institute of Technology, Cambridge, Mass.

[*] Notice: The portion of the term of this patent subsequent to Jun. 26, 2001 has been disclaimed.

[21] Appl. No.: 856,749

[22] Filed: Dec. 2, 1977

Related U.S. Application Data

[63] Continuation of Ser. No. 494,507, Aug. 5, 1974, Pat. No. 4,456,755.

[51] Int. Cl.$^4$ .................. C07D 501/00; A61K 31/545
[52] U.S. Cl. ..................................... 540/228; 540/222; 540/223; 540/224; 540/225; 540/226; 540/227; 540/229; 540/230
[58] Field of Search ....................... 544/16, 22, 24, 25, 544/26, 27, 28, 29, 30

[56] References Cited

U.S. PATENT DOCUMENTS

| | | | |
|---|---|---|---|
| 3,962,224 | 6/1976 | Christensen et al. | 544/16 |
| 3,976,641 | 8/1976 | Hoover et al. | 544/30 |
| 4,020,057 | 4/1977 | Gleason | 544/26 X |
| 4,134,734 | 12/1978 | Gleason | 544/26 |
| 4,158,733 | 6/1979 | Gleason | 544/29 |
| 4,218,564 | 8/1980 | Gleason | 544/26 |
| 4,236,001 | 11/1980 | Gleason | 544/26 |

FOREIGN PATENT DOCUMENTS 49-05993 1/1974 Japan.
49-49982 5/1974 Japan.

OTHER PUBLICATIONS

Sheehan, et al., J. Org. Chem. vol. 39, No. 10, pp. 1444–1445, 5/17/74.
Hauser, et al., Helv. Chim Acta. vol. 50, pp. 1327–1335, (1967).
Morin, et al., "Chemistry of Cephalosporin Antibiotics," Progress in the Chemistry of Organic Natural Products XXVIII, Wien, Springer-Verlag (1970).
Kaiser, et al., "Modifications of the Betalactam System", Flynn ed. *Cephalosporins & Penicillins*, Academic Press, pp. 118–119, (1972).
Nazler, "Advances in Penicillin Research", *Adv. Drug Research*, Academic Press, vol. 7, pp. 72–73, (1973).

*Primary Examiner*—Donald G. Daus
*Assistant Examiner*—Diana G. Rivers
*Attorney, Agent, or Firm*—George W. Neuner; David G. Conlin

[57] ABSTRACT

In accordance with this invention, it has been found that the oxygen analog of 7-amino-cephalosporanic acid and biologically active derivatives thereof can be formed from esters of 7-amino-cephalosporanic acid. Esters of 7-oxocephalosporanic acid can be formed by diazotization of an ester or 7-amino-cephalosporanic acid and contact of the diazo compound so formed with a hypohalous acid and a base in a water miscible organic solvent. Oxygen analogs of 7-aminocephalosporins isolated as esters are then formed by reducing the aforesaid ester to the corresponding 7β-hydroxy-cephalosporanate and then forming the desired analog by introduction of a side chain via hydroxyl group modification. Oxygen analogs of 7-amino-cephalosporins are then formed by regeneration of the acid via protective group removal.

6 Claims, No Drawings

OXYGEN ANALOGS OF CEPHALOSPORINS

This is a continuation of application Ser. No. 494,507 filed Aug. 5, 1974 now U.S. Pat. No. 4,456,755.

BACKGROUND OF THE INVENTION

1. Introduction

This invention relates to derivatives of cephalosporin and more particularly, to oxygen analogs of 7-aminocephalosporanic acid and biologically active derivatives thereof.

2. Description of the Prior Art

Following the discovery of the penicillins and their synthesis, perhaps one of the most important advances in medical research was the discovery of the cephalosporin antibiotics and their use in clinical medicine. The cephalosporin antiobiotics, though not penicillins, have a structure quite similar to the structure of the penicillins and the two can be coproduced in the fermentation of a cephalosporium organism. Because of this similarity in structure and a similarity in chemical reactivity, considerable research has been devoted to the formation of derivatives of cephalosporins using, to a large extent, chemical reactions useful for the formation of penicillin derivatives. For example, 7-aminocephalosporanic acid (7-ACA) may be obtained by mild acid hydrolysis of Cephalosporin C. The 7-ACA compound is then available for formation of a multitude of derivatives. For example, reacylation of 7-ACA with phenylacetyl chloride gives a derivative that has antibacterial activity approximately 100-fold greater than Cephalosporin C. Many other reactions of the amino group of 7-ACA are known and reported in the literature. Thus, acyl groups, isocyanates, isothiocyanates, halogen compounds, methylisoureas, ethylene oxide, ethylene imine and the like have been introduced into the 7-amino group of 7-ACA to form both biologically active and biologically inactive derivatives.

In addition to the above, there have been reactions of both the β-lactam ring system and the dihydrothiazine ring system of the cephalosporins. For example, with regard to the β-lactam ring system, C-7 epimers may be formed by treatment of cephalothin sulfoxide with triethylamine in refluxing chloroform. With regard to the dihydrothiazine ring system, there is the possibility of reaction of the double bond, the C-3 substituents and the carboxyl group to form a vast number of derivatives.

Reactions of the cephalosporins, as described above, are reported in part by R. B. Morin and B. G. Jackson, "Chemistry of Cephalosporin Antibiotics", Progress in the Chemistry of Organic Natural Products XXVIII, Wein, Springer-Verlag, 1970.

For brevity, the commonly accepted abbreviation "7-ACA" will be used for the term 7-aminocephalosporanic acid throughout the balance of this specification.

SUMMARY OF THE INVENTION

The present invention provides a wide variety of new derivatives of the cephalosporins and is based upon the discovery of certain esters of 7-oxocephalosporanic acid and methods for the formation of said esters. The esters of this invention are intermediates useful for the formation of the biologically active oxygen analog (7β-hydroxycephalosporanic acid) of 7-ACA. This oxygen analog may be used to form a wide variety of biologically active derivatives analogous to the derivatives of the 7-ACA. Thus, the invention provides novel esters of 7-oxocephalosporanic acid, the oxygen analog to 7-ACA, derivatives of said oxygen analog and methods for the formation of the aforesaid.

The esters of 7-oxocephalosporanic acid are formed by esterifying the acid group of 7-ACA with a pharmaceutically acceptable blocking group, diazotization of the amino group, and contact of the diazo compound so formed with a hypohalous acid and a base in a water miscible organic solvent.

The oxygen analog of 7-aminocephalosporanate is formed by reducing the aforesaid ester to a corresponding 7β-hydroxycephalosporanate. Thereafter, derivatives of the oxygen analog can be formed by any suitable hydroxyl group modification reaction such as acylation or other derivatizations analogous to those of 7-aminocephalosporanate. The pharmaceutically acceptable blocking group can then be removed regenerating the free acid.

DESCRIPTION OF THE PREFERRED EMBODIMENTS

The first step in the formation of the esters of 7-oxocephalosporanic acid is the formation of an ester of 7-ACA by an esterification reaction whereby the carboxyl group is protected with a pharmaceutically acceptable blocking group. This is necessary to prevent reaction through the reactive carboxyl group which could interfere with the desired reaction.

The formation of such an ester is a well known procedure and is common practice in the art. It is used in the formation of derivatives of 7-ACA as well as in the formation of derivatives of 6-amino penicillanic acid (6-APA). Preferably, for purposes set forth herein, the benzhydryl ester is formed by reaction with diphenyldiazomethane, though any other pharmaceutically acceptable blocking group may be used provided the group is readily removable when desired.

Using the benzhydryl ester for purposes of illustration only, the ester of 7-ACA is diazotized by contact for between 10 and 60 minutes with nitrous acid, generated most conveniently by addition of a nitrite salt to an acidified solution of the amine. Common nitrite salts, $MNO_2$, include but are not limited to salts where M is potassium, sodium, ammonium or the like. Most common acids including perchloric, sulfuric, sulfonic, haloic and tetrafluoroboric, etc. have found use in this acidification. Alkyl nitrites such as isoamyl nitrite alone or in combination with trifluoroacetic acid are employed as diazotization agents in anhydrous organic media. This reaction is performed in a solution preferably cooled below ambient temperature, more preferably to about 0° C. The diazo compound is isolable by extraction followed by drying and concentrating the extract until only the oily diazo compound remains.

The diazo compound is converted to the ketone—e.g. a 7-oxocephalsporanate by contact with about an equimolar amount of a hypohalous acid dissolved in a water miscible organic solvent containing a base. Preferably, the reaction is cooled down to a temperature of no more than room temperature and more preferably, to a temperature within the range of from 0° C. to −25° C. The time of reaction should not exceed two hours and typically requires from about 15 minutes to 45 minutes.

Hypohalous acids for use in the above transformation may be conveniently generated in situ via hydrolysis of N-Haloamides. The N-haloamide used preferably conforms to the formula

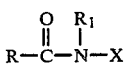

where X is halogen, preferably chlorine or bromine, and most preferably bromine. Iodine and fluorine are uncommon in this reaction and consequently less preferred. R and $R_1$ are not critical and may be selected from the group of hydrogen, a hydrocarbon radical having up to about 8 carbon atoms such as methyl, ethyl, propyl and the like, aryl or acylradicals together, or $R_2$ and $R'$ may form part of a heterocyclic ring system having up to a total of six atoms. Examples of N-haloamides within the scope of the invention include N-bromoacetamide, N-chloroacetamide, N-bromosuccinamide, N-chlorosuccinamide and the like.

The mechanism of this reaction is proposed to be as follows

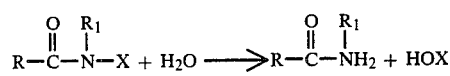

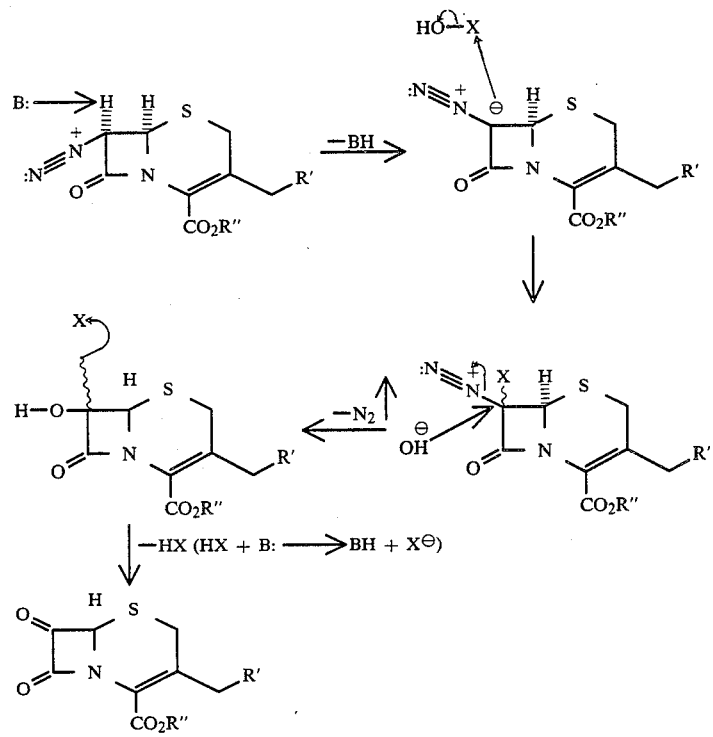

Hypohalous acid is generated upon hydrolysis of an N-haloamide. This reactant is both a source of halonium ion to effect α halogenation and also of hydroxide ion for solvolytic displacement of $N_2$. The unstable hydroxyhalo intermediate is transformed to the 7-oxocephalosporanate via rapid elimination of hydrohalic acid. This acid is neutralized by the base present in the reaction mixture.

The base employed in this neutralization can be any common organic or inorganic base known in the art. Examples of bases used within the scope of this invention include sodium bicarbonate, sodium carbonate, pyridine, dimethyl aniline and the like.

In the aforesaid reaction, the reactants are dissolved in a suitable organic solvent to which water in an amount of at least 5%, and preferably from 10 to 35%, by volume of solvent has been added. The water is necessary for formation of the ketone. The organic solvent is not critical provided it is a solvent for the reactants, is water miscible to the extent that water is present, and is non-reactive with the reactants. Organic solvents such as but not limited to dimethylformamide, dimethyl sulfoxide, acetone, tetrahydrofuran and dioxane are suitable solvents for this purpose.

The reaction sequence for the formation of the ester of 7-oxocephalosporanic acid, using the benzhydryl ester as an example, for purposes of illustration only, is as follows:

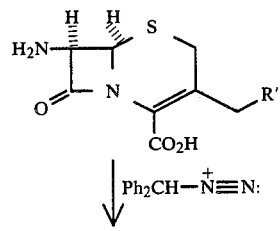

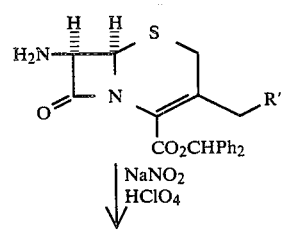

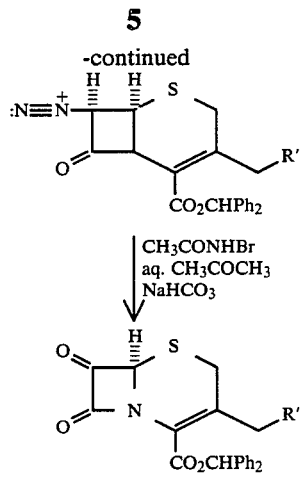

R' in the above reaction sequence will be defined below.

As noted above, the aforesaid reaction sequence for the formation of the benzhydryl 7-oxocephalosporanate may be used for the formation of other esters of 7-oxocephalosporanic acid by using a different pharmaceutically acceptable blocking group. In this respect, for purposes of this invention, a general formula for the ester of 7-oxocephalosporanic acid is as set forth below:

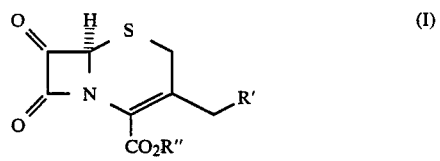

where R' is an organic nucleophile selected from the group of hydrogen, halogen, hydroxyl, alkoxyl, aryloxyl, alkylamino, arylamino, carboxylate, carbonyl, sulfonate, carbamyl, thiocarboxylate and other analogous functionalities. R" represents a pharmaceutically acceptable, readily removable protective group. Such groups include: (1) alkyl, cycloalkyl, aryl, alkaryl and aralkyl as illustrated by methyl, benzyl, p-nitrobenzyl, p-methoxybenzyl, benzhydryl and $\beta,\beta,\beta$-trichloroethyl, (2) phenacyl with or without substitution on the ring such as p-methoxyphenacyl and 2,5-dimethoxyphenacyl, (3) salts such as sodium, potassium, N-ethylpiperidine and dicyclohexylamine and (4) organo silicon groups such as trimethyl silyl. It should be understood that some of the aforesaid groups may be more difficult to remove than others, but most are groups heretofore used as protective groups in analogous reactions for both penicillins and cephalosporins and are removed in accordance with recognized procedures dependent upon the particular group involved.

The 7β-oxygen analog of 7-ACA is formed by reduction of the ester of 7-oxocephalosporanic acid (I) above. Reduction of such a reactive α diketone can be accomplished by myriad technique well known in the art. Such reducing agents include potassium borohydride, sodium borohydride, alkylated borohydrides, lithium aluminum hydride and its alkylated derivatives, well known hydrogenation catalysts, zinc dust in acetic acid and the like. The reduction is preferably carried out in an aqueous alcoholic solution at room temperature or below—e.g., down to about 0° C. The blocking group can be readily removed thereby forming the free acid by such procedures as hydrogenation or hydrolysis with trifluoracetic acid (TFA) or by using other methods known to the art. The reaction sequence for forming the 7β hydroxycephalosporic acid from 7-oxocephalosporanate ester for illustration purposes only is as follows:

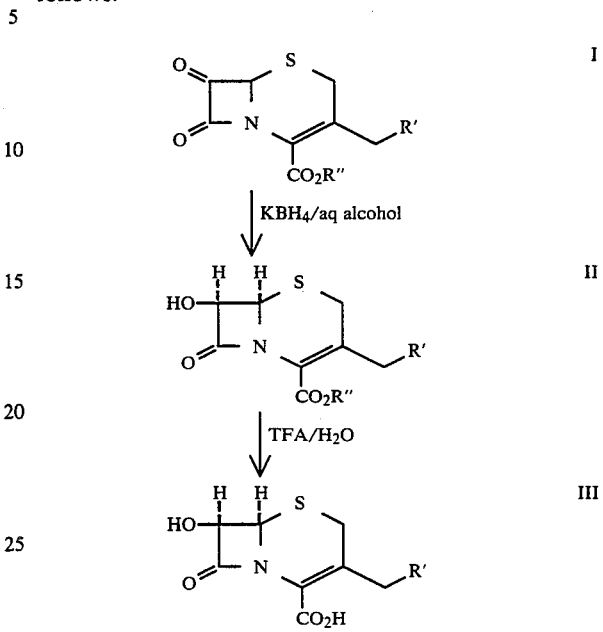

The free acid (III) is the oxygen analog of 7-ACA. It is biologically active which is unexpected since prior art had taught that a β Nitrogen substituent was essential to this activity.

Both the ester of 7β-hydroxycephalosporanic acid (II) and the acid itself (III) can be used for the formation of other biologically active derivatives of 7-ACA. In this respect, a wide variety of functional groups can be introduced into the hydroxyl group thus making it possible to produce a wide variety of oxygen analogs of cephalosporin. In this respect, typical side chain modifications include for example, formyl, acetyl, phenylacetyl, phenoxyacetyl, carbomethoxy, carbobenzyloxy, p-nitrocarbobenzyloxy, carbophenoxy, p-chlorocarbophenoxy, methanesulfonyl, benzylsulfonyl, p-chlorobenzylsulfonyl, phenylsulfonyl, or p-aminophenylsulfonyl. Although the halide, especially chloride and bromide, or anhydride of the functionalizing agent is particularly suitable for this modification, other agents may also be used. Such agents include mixed anhydrides, acid azides, lactones, particularly β-lactones, "activated esters" such as thiol esters and phenolic esters, carboxylic acids with carbodiimides or alkoxyacetylenes, thiolactones, particularly β-thiolactones, and acylated enols.

Other groups can also be introduced into the hydroxy group of (II) or (III) to provide additional types of oxygen analogs by means of such reagents as: isothiocyanates, for example, phenylisothiocyanate and ethylisothiocyanate, to convert the hydroxy group to a substituted thiocarbamate, reactive halogen compounds, such as triphenylmethyl chloride which forms the trityl ether derivative; methylisourea which converts the hydroxyl group to an isourea group; ethylene oxide and ethyleneimine, which add to the hydroxyl group with ring opening and others known to the art. Further exemplification of the above and additional groups can be found by reference to Naylor, Proc. R.

Soc. Lond, B 179, pp. 357-367, 1971, wherein reactions of 6-aminopenicillanic acid are described. These are very analogous to the reactions of 7-hydroxycephalosporanic acid.

With further reference to the above reaction scheme, it should be noted that the free acid (III) can be esterified in conventional manner to further alter the structure of the derivatives such as by formation of the methyl ester by reaction with diazomethane. Thus, by selection of the appropriate functionalization agent for reaction with the hydroxyl group and with the carboxyl group of 7β-hydroxycephalosporanic acid (III), a multitude of derivatives of the oxygen analogs can be formed having the formula:

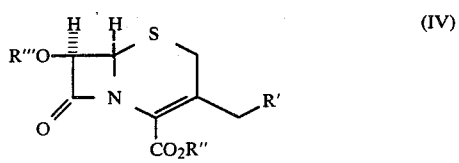

where R' and R" are as above defined. R" is an organic electrophile produced during the β hydroxy modifications defined above.

Specific examples of R' and R" are set forth below in the following table:

R'

—H, —Cl, —Br, —OH, —O—CH₃, O—C(=O)—CH₃,

—O—CH₂—CH₃, —O—C₆H₅

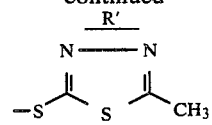

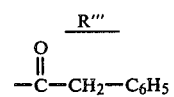

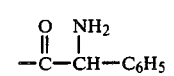

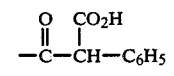

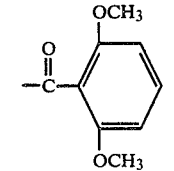

-continued

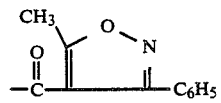

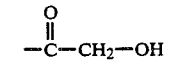

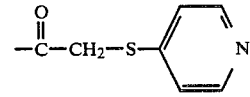

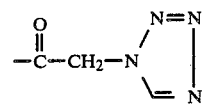

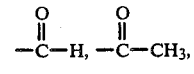

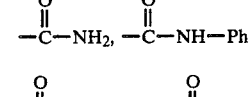

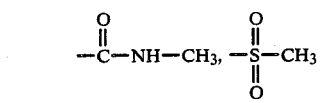

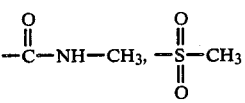

EXAMPLE 1

Benzhydryl 7-aminocephalosporanate

A suspension of 7-ACA (13.6 g, 0.05 mole) in methanol (20 ml) and dichloromethane (70 ml) was stirred overnight with diphenyldiazomethane (15.7 g) prepared according to the method set forth in Fieser and Fieser, *Organic Reagents*, pg. 338, Wiley Interscience, 1967. The violet color was discharged at the end of the reaction. Ethyl ether (200 ml) was added to precipitate the unreacted 7-ACA. Filtration and evaporation of the solvents gave a crystalline product which was recrystallized from a mixture of dichloromethane and ethyl ether. The first crop weighed 9.5 g (43%) and had the following properties: mp. 128.5–129.5; nmr (DCCl$_3$, ppm): 7.39 (S, 10H), 7.00 (S, 1H), 5.19–4.62 (M, 4H), 3.50 (D, 2H), 2.05 (S, 3H), 1.84 (S, br, 2H); ir (film, cm$^{-1}$): 3400, 1770, 1730, 1655, 1390, 1225.

EXAMPLE 2

Benzhydryl 7-diazocephalosporanate

Benzhydryl 7-aminocephalosporanate prepared as in Example 1 (3 g, 6.85 mole) was dissolved in dichloromethane (90 ml) and stirred at 0° C. Sodium nitrite (0.7 g, 1.5 eg), dissolved in H$_2$O (10 ml), was added to the cooled stirred solution and 1.01N perchloric acid (10.5 ml, 1.5 eg.) was added dropwise. The mixture was stirred at 0° C. for 1 hr. and diluted with additional dichloromethane, washed twice with ice cold water and once with an ice cold sodium chloride solution. The dichloromethane layer was then dried and evaporated to a yellow oil. It had the following properties: nmr (DCCl$_3$, ppm): 7.39 (S, 10H), 7.00 (S, 1H), 5.40 (S, 1H), 5.08–4.52 (Q, 2H), 3.35 (S, br, 2H), 1.98 (S, 3H); ir (film cm$^{-1}$): 2090, 1780, 1735, 1235.

EXAMPLE 3

Benzhydryl 7-oxocephalosporanate

Benzhydryl 7-diazocephalosporanate prepared from 3 g of benzhydryl 7-aminocephalosporanate in the manner of Example 2 was used without further purification. It was dissolved in a 10% aq. acetone (90 ml) solution and cooled in an ice-acetone-sodium chloride bath (−15° C.). Sodium bicarbonate (3 g) and N-bromoacetamide (0.945 g) were poured into the stirred cold solution. After 45 minutes, the reaction mixture was diluted with dichloromethane and water. Extraction with dichloromethane was repeated three times. The organic layer was washed once with cold water and once with cold sodium chloride solution. Drying and evaporation of solvent gave about 3 g of yellow oil which was purified by column chromatography on silicic acid and eluted with 1:9 ethyl etherdichloromethane. The yield was 50% from benzhydryl 7-aminocephalosporanate. The properties were as follows: nmr (DCCl$_3$, ppm): 7.39 (S, 10H), 7.00 (S, 1H), 5.21 (S, 1H), 5.10–4.65 (Q, 2H), 3.48 (Q, 2H), 2.01 (S, 3H); ir (film, cm$^{-1}$): 1825, 1785, 1730, 1230.

EXAMPLE 4

Benzhydryl 7β-hydroxycephalosporanate

Crude benzhydryl 7-oxocephalosporanate (2.95 g) was dissolved in ethanol (150 ml). To this cooled and stirred solution, there was added a solution of potassium borohydride (0.74 g) in a 1:1 ethanol-water mixture (150 ml). The reaction was quenched after 2 minutes by addition of 1N HCl to pH 2. The reaction mixture was diluted with water and extracted twice with dichloromethane. The organic layer was washed once with sodium bicarbonate solution and once with sodium chloride solution. Drying and evaporation gave a yellow oil which was chromatographed to give 1.2 g solid product. The product was recrystallized from benzene. Its properties are as follows: mp 122°–3°; nmr (DCCl$_3$, ppm): 7.39 (S, 10H), 7.00 (S, 1H), 5.29 (d, 1H, J=4.5 hz), 5.20–4.62 (m, 3H, J=4.5 and 13 hz), 3.90 (S, br., 1H)' 3.45 (d, 2H), 2.04 (S, 3H); ir (CH$_2$Cl$_2$, cm$^{-1}$): 3540, 1785, 1735, 1225.

EXAMPLE 5

7β-hydroxycephalosporanic acid

Benzhydryl 7β-hydroxycephalosporanate (0.3 g, 0.68 m moles) was dissolved at 0° C. in a mixture of trifluoroacetic acid (7 ml) and anisole (1 ml). After 1 hr., the solvents were evaporated under vacuum. The residual yellow material was washed with petroleum ether and then dissolved in ethyl acetate. Treatment with charcoal for half an hour and evaporation of the solvent gave a solid product, 0.17 g (99%). It was recrystallized from ethyl acetate. Its properties were as follows: mp 132° (decomp). nmr (acetone d$_6$, ppm): 5.40 (d, 1H, J=4.8 Hz), 5.15–4.80 (m, 3H, J=4.8 and 13 Hz), 3.55 (d, 2H), 2.04 (S, 3H); ir (KBr, cm$^{-1}$): 3430, 3100, 1780–1700, 1625, 1380, 1220. Bioassay results (minimum inhibitory concentration in Mg/ml): S.aureus (75), B subtilis (75) E.coli (50), K. Pneumoniae (200).

EXAMPLE 6

Benzhydryl 7β-phenoxyacetoxycephalosporanate

Benzhydryl 7β-hydroxycephalosporanate (0.8 g), (1.82 m moles) and phenoxyacetyl chloride (0.42 g, 1.5 eq.) were dissolved in dichloromethane (50 ml). Pyridine (0.15 ml, 1.5 eq.) was added to the cooled stirred solution. After stirring for three hours at room temperature, the dichloromethane solution was washed with water, sodium bicarbonate solution, and sodium chloride solution. Drying and evaporation gave a yellow oily product which was chromatographed on silicic acid using a 1:20 ethyl ether/dichloromethane mixture to yield 0.85 g of a pale yellow oil, 88% yield. Its properties are as follows: nmr (DCCl$_3$, ppm): 7.54–6.80 (m, 16H), 6.10 (d, 1H, J=4.8 Hz), 5.20–4.65 (q, 3H, J=4.8 and 14 Hz), 4.75 (S, 2H), 3.38 (S, br., 2H), 1.98 (S, 3H); ir (film, cm$^{-1}$): 1785, 1730, 1600, 1495, 1380, 1225.

EXAMPLE 7

7β phenoxyacetoxycephalosporanic acid

The procedure of Example 5 was repeated with a product yield of 93%, the product having the following properties: nmr (acetone-d$_6$, ppm): 8.10 (br, 1H), 7.42–6.87 (m, 5H), 6.32 (d, +H, J=4.8 H$_z$), 5.25 (d, 1H, J=4.8 Hz), 5.28–4.70 (q, 2H, J=14 H$_z$), 4.92 (S, 2H), 3.60 (d, 2H), 2.02 (S, 3H): ir (film, cm$^{-1}$): 3580, 3520–2500, 1785–1690, 1635, 1600, 1495, 1380, 1230. Bioassay results (minimum inhibitory concentration in Mg/ml): S.aureus (12.5), B.subtilis (25), E.Coli (200), K. pneumoniae (200).

EXAMPLE 8

Benzhydryl 7β-(2-thienyl)acetoxycephalosporanate

Benzhydryl 7β-hydroxycephalosporanate (0.45 g, 1.02 m moles), 2-thienylacetic acid (0.21 g, 1.5 eq.), and pyridine (0.1 ml–1.2 eq.) were dissolved in dichloromethane (50 ml) at 0°. To this solution was added diisopropyl carbodiimide (0.13 g–1 eq.). The cold solution was stirred one hour and then allowed to stand 17 hours under refrigeration. The solid urea formed was separated by filtration and the filtrate was diluted with dichloromethane and washed with cold dilute hydrochloric acid, sodium bicarbonate solution, and sodium chloride solution. Drying and evaporation gave a yellow oil which was chromatographed on silicic acid in a 1:20 mixture of ethyl ether and dichloromethane to yield 0.6 g product (>95%) having the following properties: nmr (DCCl₃ ppm): 7.54–6.90 (m, 14H), 6.05 (d, 1H, J=4.8 Hz), 5.20–4.60 (d on q, 3H, J=4.8 Hz and 14 Hz, 3.91 (S, 2H), 3.36 (S, br, 2H), 1.98 (S, 3H); ir (film, cm⁻¹): 1785, 1330, 1360, 1235.

EXAMPLE 9

7β (2-thienyl)acetoxycephalosporanic acid

The procedure of Example 5 was used to yield a product obtained by freeze drying from benzene. The yield was 98% and the product had the following properties: nmr (DCCl₃, ppm): 7.73 (S, br, 1H), 7.40–7.20 (m, 2H), 7.00 (d, 1H), 6.19 (d, 1H, J=4.8 Hz), 5.38–4.82 (d on q, 3H, J=4.8 Hz and 15 Hz), 4.00 (S, 2H), 3.48 (S, br., 2H), 2.13 (S, 3H); ir (film, cm⁻¹): 3560–2540, 1780, 1725, 1380, 1225. Bioassay results (minimum inhibitory concentration in Mg/ml): *S aureus* (12.5), *S. fecalis* (200), *B. subtilis* (6.25), *P. Mirabilis* (200), *P. vulgaris* (200), *K. pneumoniae* (100).

We claim:

1. A compound of the formula

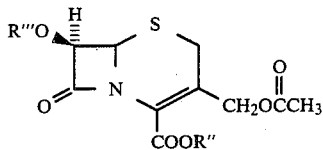

wherein:
R″ is hydrogen, methyl, benzyl, phenacyl, β,β,β-trichloroethyl or benzhydryl; and
R‴ is hydroxyacetyl, phenoxyacetyl, phenylacetyl, tetrazolylacetyl or 2-thienylacetyl.

2. A compound of the formula:

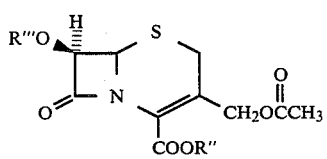

wherein:
R″ is hydrogen or benzhydryl; and
R‴ is phenoxyacetyl or 2-thienylacetyl.

3. A compound of the formula:

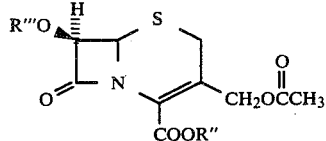

wherein:
R″ is hydrogen, methyl, benzyl, phenacyl, β,β,β-trichloroethyl or benzhydryl; and
R‴ is hydrogen, hydroxyacetyl, phenoxyacetyl, phenylacetyl, tetrazolylacetyl or 2-thienylacetyl.

4. A compound of the formula:

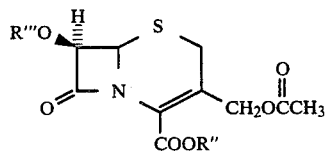

wherein:
R″ is hydrogen or benzhydryl; and
R‴ is hydrogen, phenoxyacetyl or 2-thienylacetyl.

5. A compound of the formula:

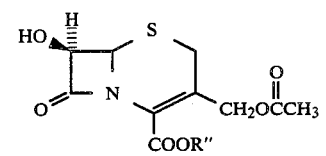

wherein:
R″ is hydrogen, methyl, benzyl, phenacyl, β,β,β-trichloroethyl or benzhydryl.

6. A compound of the formula:

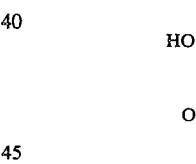

wherein:
R″ is hydrogen or benzhydryl.

* * * * *